United States Patent
Franco Puntes et al.

(10) Patent No.: US 9,023,370 B2
(45) Date of Patent: May 5, 2015

(54) CONJUGATES COMPRISING NANOPARTICLES COATED WITH PLATINUM CONTAINING COMPOUNDS

(75) Inventors: Victor Franco Puntes, Barcelona (ES);
Fernando Domínguez Puente, Teo (ES);
Francisco Manuel Romero Martínez, Valencia (ES); Óscar Gallego Rubio, Barcelona (ES)

(73) Assignees: Fundacio Privada Institut Catala de Nanotecnologia, Bellaterra (Barcelona) (ES); Institucio Catalana de Recerca I Estudis Avancats, Barcelona (ES); Universidade de Santiago de Compostela, Santiago de Compostela (ES); Universitat de Valencia, Valencia (ES); Fundacio Institut de Recerca de l'Hospital de la Santa Creu J Sant Pau, Barcelona (ES)

( * ) Notice: Subject to any disclaimer, the term of this patent is extended or adjusted under 35 U.S.C. 154(b) by 309 days.

(21) Appl. No.: 13/140,347

(22) PCT Filed: Dec. 15, 2009

(86) PCT No.: PCT/EP2009/067136
§ 371 (c)(1),
(2), (4) Date: Jul. 8, 2011

(87) PCT Pub. No.: WO2010/069941
PCT Pub. Date: Jun. 24, 2010

(65) Prior Publication Data
US 2011/0262500 A1    Oct. 27, 2011

(30) Foreign Application Priority Data
Dec. 16, 2008   (EP) ..................... 08171870

(51) Int. Cl.
*A61K 9/14*      (2006.01)
*C07F 19/00*     (2006.01)
(Continued)

(52) U.S. Cl.
CPC ............. *A61K 47/48861* (2013.01); *B82Y 5/00* (2013.01)

(58) Field of Classification Search
CPC ..................... A61K 47/48861; B82Y 5/00
USPC .......................................... 424/400; 514/495
See application file for complete search history.

(56) References Cited

U.S. PATENT DOCUMENTS

2006/0099146 A1    5/2006   Chow et al.
2006/0222595 A1    10/2006  Mukherjee et al.
(Continued)

FOREIGN PATENT DOCUMENTS

EP   0174114    3/1986
JP   6187692 A  6/1986
(Continued)

OTHER PUBLICATIONS

Socorro Vázquez-Campos et al.(Gold Nanoparticles as carriers of cisplatin: A new approach for cancer treatment, Trends in Nanotechnology Conference, Sep. 1, 2008, abstract, submitted by Applicant on Nov. 8, 2011).*

(Continued)

*Primary Examiner* — Janet Epps-Smith
*Assistant Examiner* — Courtney Brown
(74) *Attorney, Agent, or Firm* — Peter B. Scull; Hamilton, DeSanctis & Cha LLP

(57) ABSTRACT

The present invention relates to conjugates of formula (I) having colloidal stability in a medium, wherein NP is a gold, silver or platinum nanoparticle; L is a linker selected from the group consisting of formula (II), formula (III), and a stereoisomer of any of the formulas (II) and (III), which is attached to the nanoparticle NP through sulfur atoms; wherein the meanings of X, n, p, Y and s are further specified in the description; and A is a platinum (II) biradical selected from the group consisting of formula (IV), formula (V) and formula (VI) including any of the stereoisomers of all of them, wherein the biradical is optionally in the form of a salt and is attached to the linker L through the single bonded oxygen atoms of the carboxyl groups. It also relates to a process for the preparation of the conjugates of formula (I) and to pharmaceutical compositions containing them. The conjugates of the invention are used for the treatment of cancer.

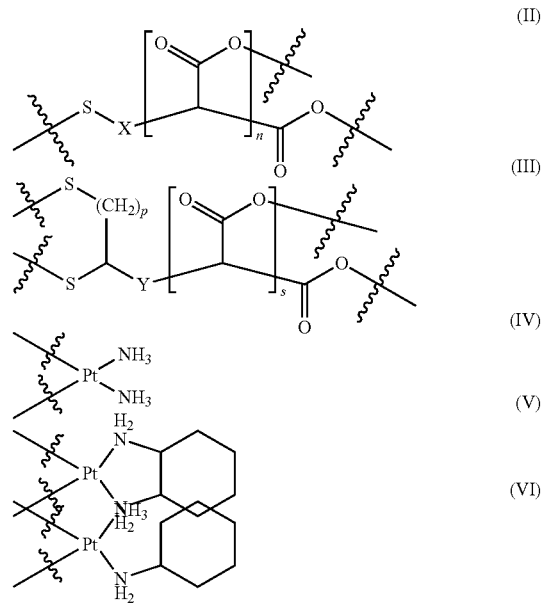

18 Claims, 8 Drawing Sheets

(51) Int. Cl.
   *A61K 31/282*   (2006.01)
   *A61P 35/00*    (2006.01)
   *A61K 47/48*    (2006.01)
   *B82Y 5/00*     (2011.01)

(56) References Cited

U.S. PATENT DOCUMENTS

2008/0003183 A1* 1/2008 Guo ............................ 424/9.42
2012/0315218 A9* 12/2012 Chen ............................ 424/9.1

FOREIGN PATENT DOCUMENTS

| JP | 2005535604 A | 11/2005 |
|---|---|---|
| WO | 03101425 A3 | 12/2003 |

OTHER PUBLICATIONS

Vàzquez-Campos et al., Gold Nanoparticles as carriers of cisplatin: A new approach for cancer treatment, Trends in Nanotechnology Conference, Sep. 1, 2008, abstract.*

Nikhil R. Jana et al., Seeding Growth for Size Control of 5-40 nm Diameter Gold Nanoparticles, Oct. 2001, pp. 6782-6786, vol. 17, No. 22, Langmuir, American Chemical Society, Washington, D.C.

Gibson et al., "Paclitaxel-Functionalized Gold Nanoparticles," American Chemical Society, J. Am. Chem. Soc. 129:11653-11661, Sep. 19, 2007.

Paciotti et al., "Colloidal Gold: A Novel Nanoparticle Vector for Tumor Directed Drug Delivery," Taylor & Francis Inc., Drug Delivery 11:169-183, May-Jun. 2004.

Ren et al., "Cisplatin-loaded Au—Au2S nanoparticles for potential cancer therapy: Cytotoxicity, in vitro carcinogenicity, and cellular uptake," Wiley Periodicals, Inc., J. Biomed. Materials Research 85A:787-796, 2008; published on-line Wiley InterScience (www.interscience.wiley.com) Sep. 26, 2007.

Ren et al., "Sythesis of nir-sensitive Au—Au2S nonocolliods for drug delivery," Elsevier Science B.V., Materials Science and Engineering C 23:113-116, 2003 (the year of publication is sufficiently earlier than the effective U.S. filing date and any foreign priority date so that the particular month of publication is not in issue).

Roux et al., "Synthesis, Characterization of Dihydrolipoic Acid Capped Gold Nanoparticles, and Functionalization by the Electroluminescent Luminol," American Chemical Society, Langmuir 21:2526-2536, Mar. 15, 2005.

Vàzquez-Campos et al, "Gold nanoparticles as carriers of cisplatin: A new approach for cancer treatment," Trends in Nanotechnology Conference—TNT2008, Oviedo Spain, Sep. 1-5, 2008.

International Search Report for International Application No. PCT/EP2009/067136, mailed Apr. 26, 2010, European Patent Office, Rijswijk, The Netherlands, 4 pages.

Extended European Search Report for European Application No. 08171870.2-1216, mailed May 25, 2009, European Patent Office,The Hague, The Netherlands, 7 pages.

Kadir Aslan, et al., Surface Modification of Colloidal Gold by Chemisorption of Alkanethiols in the Presence of a Nonionic Surfactant, May 25, 2002, pp. 6059-6065, vol. 18, No. 16, Langmuir, American Chemical Society, Washington, D.C.

Bernhardt et al., Carboplatin derivatieves with superior antitumor activity compared to the parent compound, Inorganica Chimica Actia, Aug. 20, 2004, pp. 4452-4466,vol. 357, Elsevier, Amsterdam, NL.

Sellers, et al., Structure and Binding of Alkanethiolates on Gold and Silver Surfaces: Implications for Self-Assembed Monlayers, J. Am. Chem. Soc. 1993, received Sep. 16, 1992, pp. 9389-9401, vol. 115, No. 21, American Chemical Society, New York, USA.

* cited by examiner

CONJUGATES COMPRISING NANOPARTICLES COATED WITH PLATINUM CONTAINING COMPOUNDS

CROSS-REFERENCE TO RELATED APPLICATIONS

This application is being filed under 35 USC 371 as a National Stage Application of pending International Application No. PCT/EP2009/067136 filed Dec. 15, 2009, which claims priority to parent European Patent Application No. EP 08171870.2 filed on Dec. 16, 2008 which are hereby incorporated by reference herein in their entireties for all they teach and disclose.

The present invention relates to conjugates having colloidal stability in a medium comprising metallic nanoparticles coated with platinum containing compounds. It also relates to a process for their preparation and to pharmaceutical compositions containing them. The conjugates of the invention are used for the treatment of cancer.

BACKGROUND ART

Platinum compounds play an important role in cancer chemotherapy. Cisplatin, the first generation of platinum based chemotherapy drug, is one of the most common anticancer agents and has a wide spectrum of anticancer activity. However, drawbacks such as the poor selectivity between malignant and normal cells, leading to severe toxic effects (such as nephrotoxicity, neurotoxicity and ototoxicity) and the presence of intrinsic or acquired resistance, so that the doses must be increased, importantly limit its efficacy. Moreover, cisplatin has additional drawbacks, such as low solubility in aqueous solutions and side effects such as nausea and vomiting.

Although extensive efforts were devoted to overcoming these major issues by developing new generations of platinum derivatives that are less toxic and more active than cisplatin and/or do not display cross-resistance, the improvements are still rather small. Thus, second generation platinum-based drugs, such as carboplatin or oxaliplatin, have lower renal and gastrointestinal toxicities but bone marrow toxicity caused by carboplatin and neurotoxicity of oxaliplatin are limitant. Their anticancer spectrum and efficacy are different than cisplatin.

Drug delivery systems in which carriers incorporate the drug either through chemical bonding or passive adsorption may deliver the drug to specific cells and avoid elimination by the immune system. Ideally, such delivery systems extravasate the tumor vasculature and accumulate within the tumor environment. A particle delivery system capable to release a cancer drug solely within the tumor may also reduce the accumulation of the drug in healthy tissues.

There are several drug delivery systems described in literature that are based on nanomaterials. In some cases the drug is adsorbed on the nanomaterial or encapsulated into nanocapsules. In other cases it is covalently attached to the surface of the nanomaterial.

In this context many attempts to derivate cisplatin with nanostructures have been described, such as polymeric capsules, functionalized soluble single-walled carbon nanotubes (SWNT), Nanohorns, $Fe_3O_4$ particles, or polymers such as Prolindac®, a 22 kD hydroxypropylmethacrilamide copolymer as a backbone and then a glycine chelator linker which is pH sensitive. In Ren L. et al, *Mater. Sci. Eng. C* 2003, vol. 23, pp. 113-116 and US 2006/099146 near infrared sensitive nanoparticles are described, which comprise a surfactant loaded with commercial cisplatin via electrostatic interactions. Further, the abstract of Vàzquez-Campos et al, "Gold nanoparticles as carriers of cisplatin: A new approach for cancer treatment", Trends in nanotechnology conference-TNT2008, 1 Sep. 2008, discloses cisplatin conjugated to gold nanoparticles via 11-mercaptoundecanoic acid (MUA) linkers for the treatment of cancer. In many of those systems, including the ones disclosed by Ren L. et al and Vàzquez-Campos et al, colloidal and conjugate stability in the working environment is an issue not solved.

Therefore, despite the teaching of the prior art, the research of new drug delivery systems in cancer is still an emerging field and there is a need for further exploring delivery systems which increase the relative efficacy and safety of a cancer therapy. In particular, it is of interest to find stable drug delivery systems which can transport efficiently the drug to its target.

SUMMARY OF THE INVENTION

Inventors have found that when a platinum compound is conjugated to a metallic nanoparticle through a linker via coordination bonds rendering a conjugate having colloidal stability, the resulting delivery system is capable of delivering 10 times more platinum to the tumor without increasing the toxicity to normal tissues. As a result, tumor resistance to platinum compounds is reduced and side effects are diminished. In addition, the conjugates of the invention are highly soluble in comparison with the currently used free platinum compounds, whose solubility is low.

In comparison with the strategies described in the prior art, the inventor's approach used for the preparation of the conjugates of the invention comprises both the two following properties which are required in order to have therapeutic effects: i) it controls efficiently the colloidal stability of the conjugates maximizing the therapeutic drug load and ii) provides conjugates having at the same time a pH sensitive link which makes that the drug is deactivated when attached to the nanoparticle and it only becomes active after detaching from the conjugate when encountering an acidic environment as in the endolysosome.

Therefore, a first aspect of the present invention refers to a conjugate of the formula (I)

having colloidal stability in a medium wherein

NP is a gold, silver or platinum nanoparticle;

L is a linker of formula (II) or a stereoisomer thereof, which is attached to the nanoparticle NP through the sulfur atom; or L is a linker of formula (III) or a stereoisomer thereof, which is attached to the nanoparticle NP through the two sulfur atoms

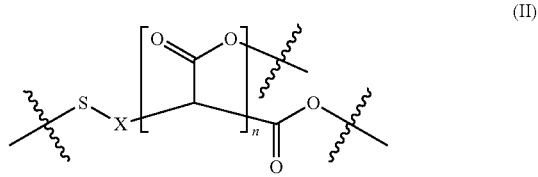

-continued

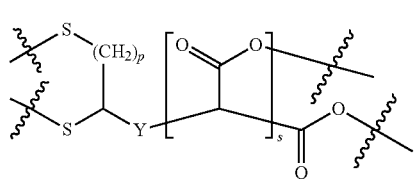

(III)

wherein:
X and Y independently represent a $(C_2-C_{20})$hydrocarbon chain, wherein at least one carbon atom is optionally replaced by a CO group or a heteroatom selected from the group consisting of O and N; and wherein the $(C_2-C_{20})$ hydrocarbon chain is optionally substituted with one or more substitutents selected from the group consisting of halogen, OH, $CONH_2$, $CO_2(C_1-C_6)$alkyl and —CHO;
n and s independently represent a value from 0 to 1;
p represents a value from 1 to 2; and
A is a platinum (II) biradical selected from the group consisting of formula (IV), formula (V) and formula (VI) including any of the stereoisomers of all of them which is attached to the linker L through the single bonded oxygen atom of the carboxyl groups, wherein the biradical is optionally in the form of a salt

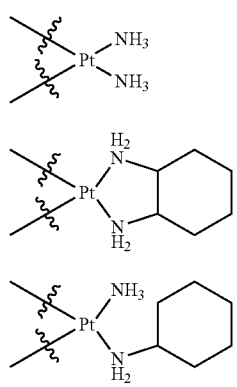

(IV)

(V)

(VI)

with the condition that:
when in the linker of formula (II) or formula (III), n=1 or s=1;
the platinum (II) biradical is attached to one molecule of linker of formula (II) or formula (III), thereby forming two COO—Pt bonds with the same linker molecule; and
when in the linker of formula (II) or formula (III), n=0 or s=0;
the platinum (II) biradical is attached to two independent linker molecules of formula (II) or formula (III), thereby forming a COO—Pt bond with each of these two linker molecules; and
being some of the linkers L of formula (II) or formula (III) in the form of free carboxyl groups.

The stable colloidal conjugates of the invention can be conveniently prepared by an appropriate conjugation method. Therefore, another aspect of the invention refers to a process for the preparation of a conjugate of formula (I) as defined above, comprising the following steps:
a) reacting a gold, silver or platinum nanoparticle NP with an excess of a compound selected from the group consisting of formula (IIa), formula (IIIa), a stereoisomer, and a salt of any of the formulas (IIa) and (IIIa), in an aqueous solution to give rise to an intermediate conjugate

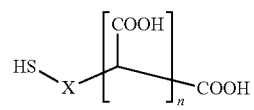

(IIa)

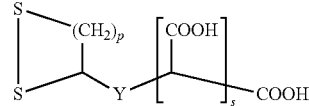

(IIIa)

wherein X, n, p, Y and s have the same meaning as defined above; and
b) reacting the intermediate conjugate obtained in step a) with an appropriate amount of a platinum (II) compound to give rise to a conjugate of formula (I) having colloidal stability, in an aqueous solution in the presence of a base, being the platinum (II) compound selected from the group consisting of formula (IVa), formula (Va), formula (VIa), and a salt of any of the formulas (IVa), (Va) and (VIa), including any of the stereoisomers of all of them.

(IVa)

$$H_2O\diagdown_{Pt}\diagup NH_3$$
$$H_2O\diagup \diagdown NH_3$$

(Va)

(VIa)

The conjugates of the present invention may be administered to mammals, including humans, suffering from a cancer. Thus, another aspect of the present invention relates to pharmaceutical compositions comprising the conjugates of formula (I) as defined above together with one or more pharmaceutically acceptable excipients.

A further aspect of the invention relates to a conjugate of formula (I) as defined above for use in cancer. Therefore, this aspect relates to the use of the conjugates of formula (I) as defined above for the manufacture of a medicament for the treatment of cancer. Alternatively, this aspect may also be formulated as a method for the treatment of cancer in a mammal, including a human, the method comprising administering to said mammal an effective amount of the previously defined conjugates of formula (I) together with one or more pharmaceutically acceptable excipients.

These aspects of the present invention will be further described in the detailed description section that follows. Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. Furthermore, the present invention covers all possible combinations of particular and preferred embodiments described herein.

BRIEF DESCRIPTION OF THE DRAWINGS

FIG. 6 not being separately shown, shows High-resolution XPS of C1s, Pt4f, Au4f, S2p and S2s spectral regions (intensity versus binding energy) showing the presence of C (FIG. 6A), S (FIG. 6B), Au (FIG. 6C) and Pt (FIG. 6D) of the conjugate of example 4.1.

DETAILED DESCRIPTION OF THE INVENTION

According to the invention, the term "conjugate" refers to a gold, silver or platinum nanoparticle which is attached to another compound which contains platinum. In particular, the term conjugate, also referred to as NP-L-A, refers to a gold, silver or platinum nanoparticle which is attached to a linker L through a pseudo-covalent bond, like the one occurring between S and Au (45 kcal/mol), and wherein the linker L is attached to a platinum compound through a coordination bond between 0 and Pt (about 4 kcal/mol). The coordination bond is not sensitive to weak variations of the pH. Thus, said coordination bonds are only hydrolyzed at pH lower than 5, thereby releasing the platinum drug. Thus, while the conjugate is stable in serum, it releases its drug load when the pH is lowered, as it occurs in the endolysosome of a tumoral cell.

The conjugates of the invention have colloidal stability in a medium. This means that the conjugates of the invention when dispersed in another medium are able to resist aggregation (i.e. precipitation). Thus, the dispersion obtained exhibits a long shelf-life and has the appearance of a solution.

The colloidal stability of the conjugates of the invention is essential since if the conjugates are not stable, they do not show any benefit either in vivo or in vitro in respect to the free drug.

In a preferred embodiment, the conjugates show colloidal stability in physiologic conditions, that is the condition or state of the body or bodily functions comprising pH close to neutral (7) and high saline concentration.

UV-Vis spectroscopy is a useful technique to determine the colloidal stability of conjugates.

Figure 2:
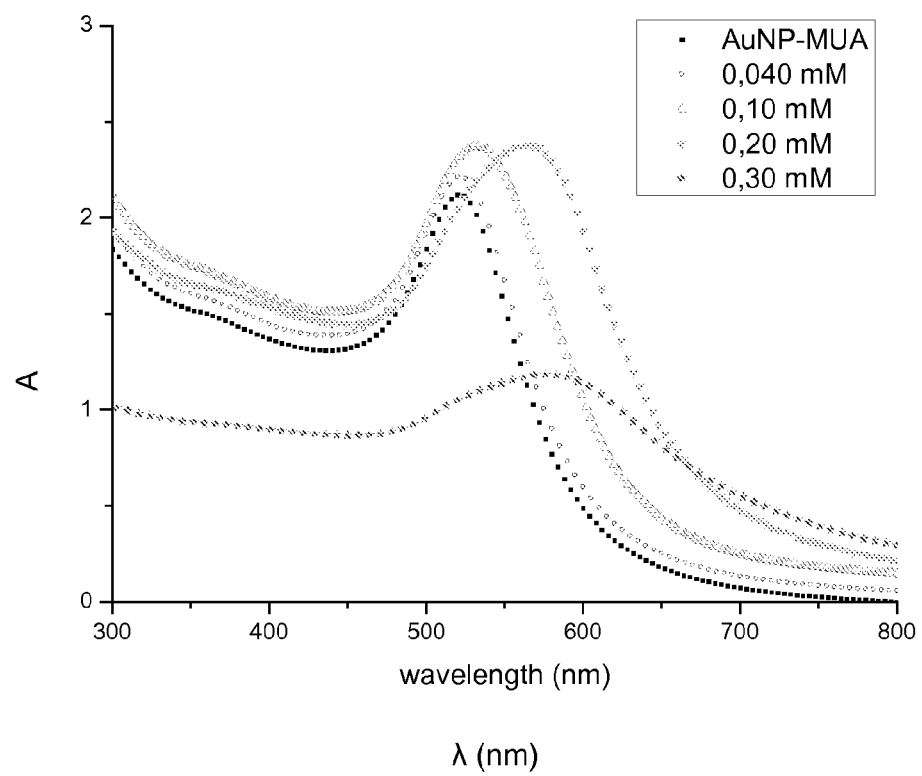
FIG. 2 shows the determination of the maximum platinum compound load per nanoparticle.

FIG. 2 shows UV-Vis spectra for several conjugates (NP: 20 nm gold nanosphere, L: 11-mercaptoundecanoic acid (MUA), A: cisplatin) each comprising a different load of the platinum compound, ranging from 0.04 mM to 0.3 mM. Irreversible aggregation (i.e. red shift and broadening of the surface plasma resonance (SPR) peak) can be seen when the concentration of the platinum compound is high enough to quench all the negative charge given by the linker shell. Thus, from 0.10 mM of cisplatin the formation of aggregates is observed and from 0.20 mM, the aggregation is irreversible, leading to precipitation of the sample.

As it will be described in detail below, in the preparation of a conjugate having colloidal stability it is key to control the number of the platinum compound molecules which are attached to the linker molecules, so that a sufficient amount of the latter remain deprotonated. Thus, the concentration of platinum compound that a conjugate can support is related to the surface charge. At the working pH the linker molecules are deprotonated and therefore charged. Generally the working pH corresponds to the pH under physiological conditions. The addition of the platinum coordination complex quenches part of that charge. This can be measured by the decrease in the ζ-potential values at a given pH. It is well known that a colloidal particle generally needs about 30 mV (positive or negative) to be stable against aggregation. This value is dependent on pH and ionic strength. The conjugates of the invention having a surface electrostatic absolute charge of at least 25 mV are also stable and also form part of the invention.

Thus, in a particular embodiment, the present invention relates to conjugates of the formula (I) having a surface electrostatic absolute charge of at least 25 mV, that is a zeta potential absolute value of at least 25 mV under physiological conditions. In another embodiment the conjugates of the formula (I) have a surface electrostatic absolute charge of at least 30 mV, that is a zeta potential absolute value of at least 30 mV under physiological conditions.

The conjugates of the invention comprise nanoparticles (also referred to herein as NPs) made of gold, silver or platinum. These metals show a high affinity towards sulfur groups (including both SH and disulfide S—S groups), such as the sulfur groups of a compound of formula (IIa) or formula (IIIa)

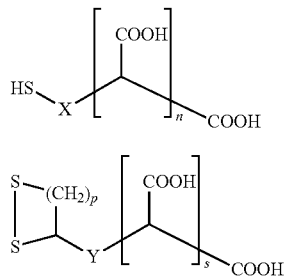

wherein X, n, p, Y and s have the meanings described above.

Thus, a free SH group or a disulfide group have a high tendency to spontaneously react with the metallic nanoparticle to form a pseudo-covalent bond metal-S. The strong binding between the linker and the nanoparticle is needed to avoid desorption of the linker molecule.

In addition, the inorganic nanoparticle is a good antenna for electromagnetic fields including for example gamma ray, X-ray, Near Infrared (NIR) or UV-Vis and microwaves).

In a preferred embodiment of the invention, gold nanoparticles (AuNPs) are used. AuNPs have a strong surface plasmon enhanced absorption and scattering making them ideal as imaging labels and contrast agents. They are not susceptible to photobleaching, biocompatible and noncytotoxic. Moreover, they can be heated when they absorb light at their resonant frequency allowing photothermal therapy of cancer.

For the purposes of the invention, the term "nanoparticles" refers to particles of nanometric size which may have different shapes and sizes. As regards the shape of the nanoparticles described herein, spheres and polyhedra comprising flat faces and straight edges are comprised within the scope of the invention. Examples of such polyhedra include, without limitation, cubes, prisms and rods. The polyhedra have the advantage that they can be near infrared (NIR)-sensitive and therefore the nanoparticles may be locally heated. In a preferred embodiment, the nanoparticles are spheres. In a preferred embodiment, the nanoparticles are gold nanospheres.

The size of the nanoparticle must be such that allows prolonged plasma life, i.e. the conjugate remains in the systemic circulation until it encounters hyperpermeable tumor capillaries.

In the case of nanospheres, the diameter is comprised in the range from 3 to 100 nm, preferably in the range from 4 to 20 nm.

In the case of nanocubes and nanoprisms, the size is defined in terms of the sphere, inscribed inside the nanocube or the nanoprism, which has the maximum diameter possible.

In both cases, the diameter of said sphere is comprised in the range from 3 to 100 nm, preferably in the range from 4 to 20 nm.

Further, in the case of rods, the size is 100 nm length and 15 nm width, preferably 45 nm length×15 nm width.

The above mentioned size values results in conjugates which are large enough to avoid the kidney, and small enough to avoid the reticuloendothelial system, part of the immune system, consisting of the phagocytic cells located in reticular connective tissue, primarily monocytes and macrophages. Moreover, this size of the conjugates of the invention (above that of essential small molecules as amino acids or small peptides) promotes endocytosis.

In a more preferred embodiment, the nanospheres of the invention have a diameter of about 10 nm. In another more preferred embodiment, the invention relates to nanocubes and nanoprisms wherein their inscribed sphere has a diameter of about 10 nm. In the most preferred embodiment, the nanoparticles of the invention are gold nanospheres having a diameter from 4 to 20 nm.

As already mentioned, the conjugates of the invention comprise a linker L selected from the group consisting of formula (II), formula (III), and a stereoisomer of any of the formulas (II) and (III),

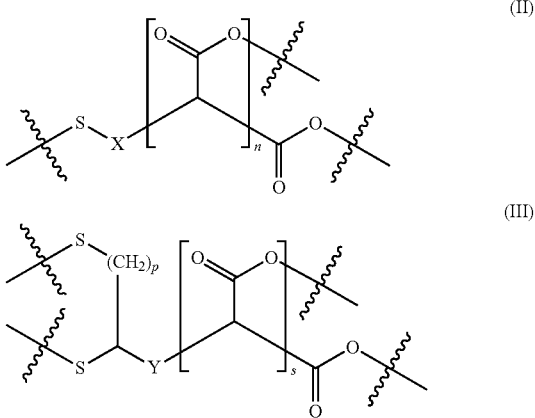

wherein X, n, p, Y and s have the meanings as previously described.

As mentioned above, in the surface charge conjugates of formula (I) NP-L-A, not all the linkers L are attached to platinum compounds but are in the form of free carboxyl groups, i.e. in the conjugates of formula (I) NP-L-A some of the platinum biradicals A do not exist. Generally, these free carboxyl groups will be deprotonated under neutral or basic conditions. In a particular embodiment, in a surface charge conjugate of formula (I) NP-L-A, at least 45% of the linkers L are in the form of free carboxyl groups, i.e. in a surface charge conjugate of formula (I) NP-L-A, at least 45% of the platinum biradicals A do not exist.

For the purposes of the present invention, the term ($C_2$-$C_{20}$) hydrocarbon chain relates to a linear or branched hydrocarbon chain comprising from 2 to 20 carbon atoms, wherein at least one carbon atom may be optionally replaced by a CO group or a heteroatom selected from the group consisting of O and N and which may optionally comprise one or more insaturations in the form of double bonds and/or triple bonds. The ($C_2$-$C_{20}$)hydrocarbon chain is optionally substituted with one or more substitutents selected from the group consisting of halogen, OH, $CONH_2$, $CO_2$($C_1$-$C_6$)alkyl and —CHO.

Further, when L is a linker of formula (II), it is attached to the nanoparticle NP through the only available sulfur atom; whereas when L is a linker of formula (III), it is attached to the nanoparticle NP through the two sulfur atoms.

In a particular embodiment, X and Y independently represent an unsubstituted $(C_2-C_{20})$hydrocarbon chain as defined above.

In a preferred embodiment, in a linker of formula (II), X represents —$(CH_2)_m$— and in a linker of formula (III), Y represents —$(CH_2)_r$—, wherein m represents a value from 2 to 10 with the condition that m+n represents a value from 2 to 10; and r represents a value from 2 to 10 with the condition that r+s represents a value from 2 to 10.

In a more preferred embodiment, in a linker of formula (II), n=0 and in a linker of formula (III), s=0. In this particular case, the linker molecule is linear and more molecules can be attached to the nanoparticle.

In a even more preferred embodiment, in the linker of formula (II), n=0 and m=10; and in the linker of formula (III), p=2, s=0 and r=4.

In the conjugates of formula (I), the linker L is further attached to a platinum (II) biradical as defined above. Thus, when L is a linker of formula (II) wherein n=1, or a linker of formula (III) wherein s=1; the platinum (II) biradical is attached to one molecule of linker, thereby forming two COO—Pt bonds with the same linker molecule. In the following scheme three conjugates are shown wherein L is a linker of formula (II) wherein n=1 and A is a platinum (II) biradical selected from the group consisting of formula (IV), (V) and (VI).

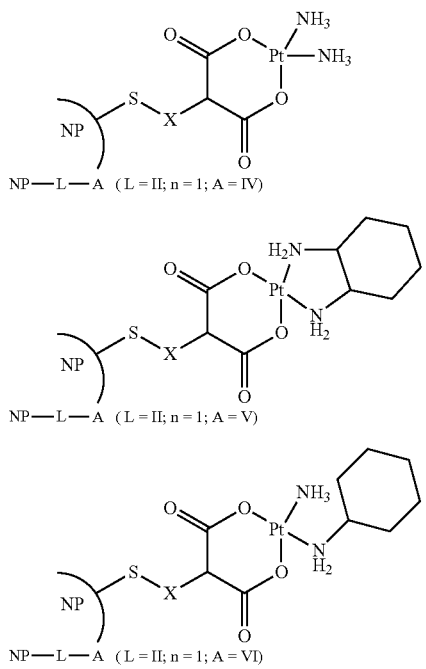

Further, when L is a linker of formula (II) wherein n=0, or a linker of formula (III) wherein s=0; the platinum (II) biradical is attached to two independent linker molecules, thereby forming a COO—Pt bond with each of these two linker molecules. In the following scheme, three conjugates are shown wherein L is a linker of formula (II) wherein n=0 and A is a platinum (II) biradical selected from the group consisting of formula (IV), (V) and (VI).

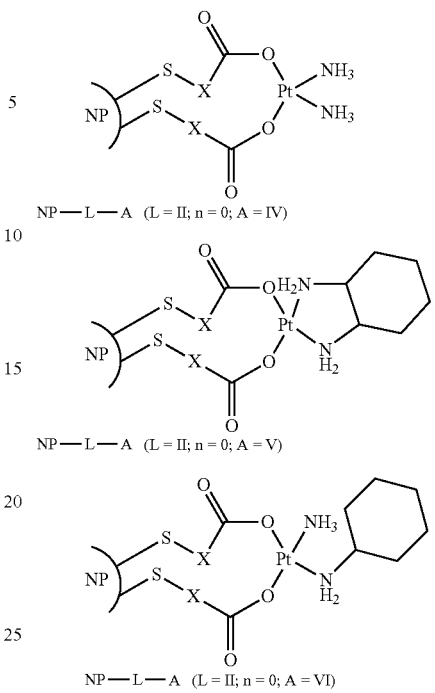

In a preferred embodiment, the conjugate of formula (I) comprises a linker of formula (II) wherein X represents —$(CH_2)_m$— or a linker formula (III) wherein Y represents —$(CH_2)_r$—, wherein m represents a value from 2 to 10 with the condition that m+n represents a value from 2 to 10; and r represents a value from 2 to 10 with the condition that r+s represents a value from 2 to 10.

In a more preferred embodiment, the conjugate of formula (I) comprises a linker of formula (II) wherein X represents —$(CH_2)_m$— and n=0, or a linker formula (III) wherein Y represents —$(CH_2)_r$— and s=0. In a even more preferred embodiment, the conjugate of formula (I) comprises a linker of formula (II) wherein X represents —$(CH_2)_m$— and n=0.

In another preferred embodiment of the invention, A represents a platinum (II) biradical of formula (IV).

In the most preferred embodiment, the conjugate of formula (I) comprises a linker of formula (II) wherein X represents —$(CH_2)_m$— and n=0 and a platinum (II) biradical of formula (IV).

The stereoisomers of the platinum biradical of formulas (IV), (V) and (VI) also form part of the invention.

The platinum biradical of formulas (IV), (V) and (VI) may form a salt together with an anion. Non-limiting examples of anions that may be present in a birradical in salt form are chloride, nitrate or hydroxide.

In the conjugate of formula (I), A is a platinum (II) biradical substantially having a cis configuration. This means that, at least 80% of the platinum (II) compounds show cis configuration.

The platinum compounds of the invention comprise two different sides as shown in the following scheme, the left side (reactive side) is designed to attach to the DNA of the cancer cells. The right side (inert side) comprising the N atoms is responsible of the bio distribution of the drug.

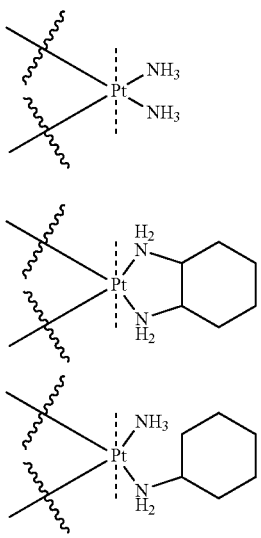

(IV)

(V)

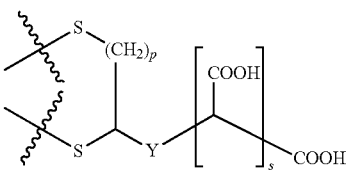

(IIIb)

or a stereoisomer or a salt of any of these linkers, such as for example the sodium salt. This first step is shown in the following scheme:

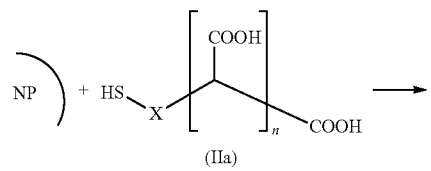

(IIa)

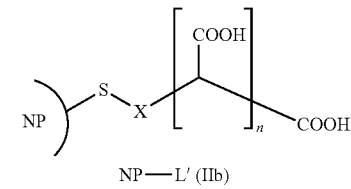

NP—L' (IIb)

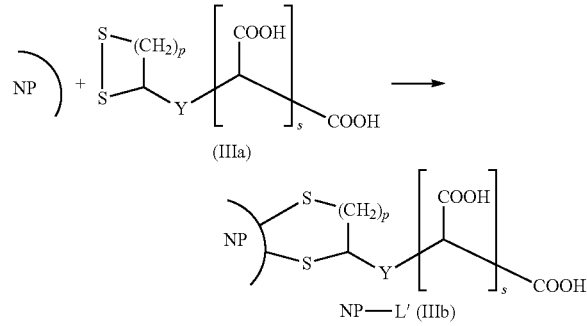

Generally, the partial functionalization of the conjugates of formula (I) with platinum compounds gives rise to a surface disorder. Packing of the molecules of platinum containing drug to the nanoparticle, specially by their reactive ends, protects the molecules from biodegradation until they are released. This fact together with the highly hydrophylicity of the COO— groups prevents opsonisation, that is, coating of the particles with special proteins called opsonins, and subsequent recognition by phagocytes and transportation into the liver. Thus, when the conjugates reach the target cells, a large amount of platinum containing drug may be administered.

Thus, the conjugates of the invention are stable in the sense that they do not precipitate in a medium as it has been mentioned above, and in the sense that the platinum containing drug does not detach from the nanoparticle in the working environment.

Figure 1:
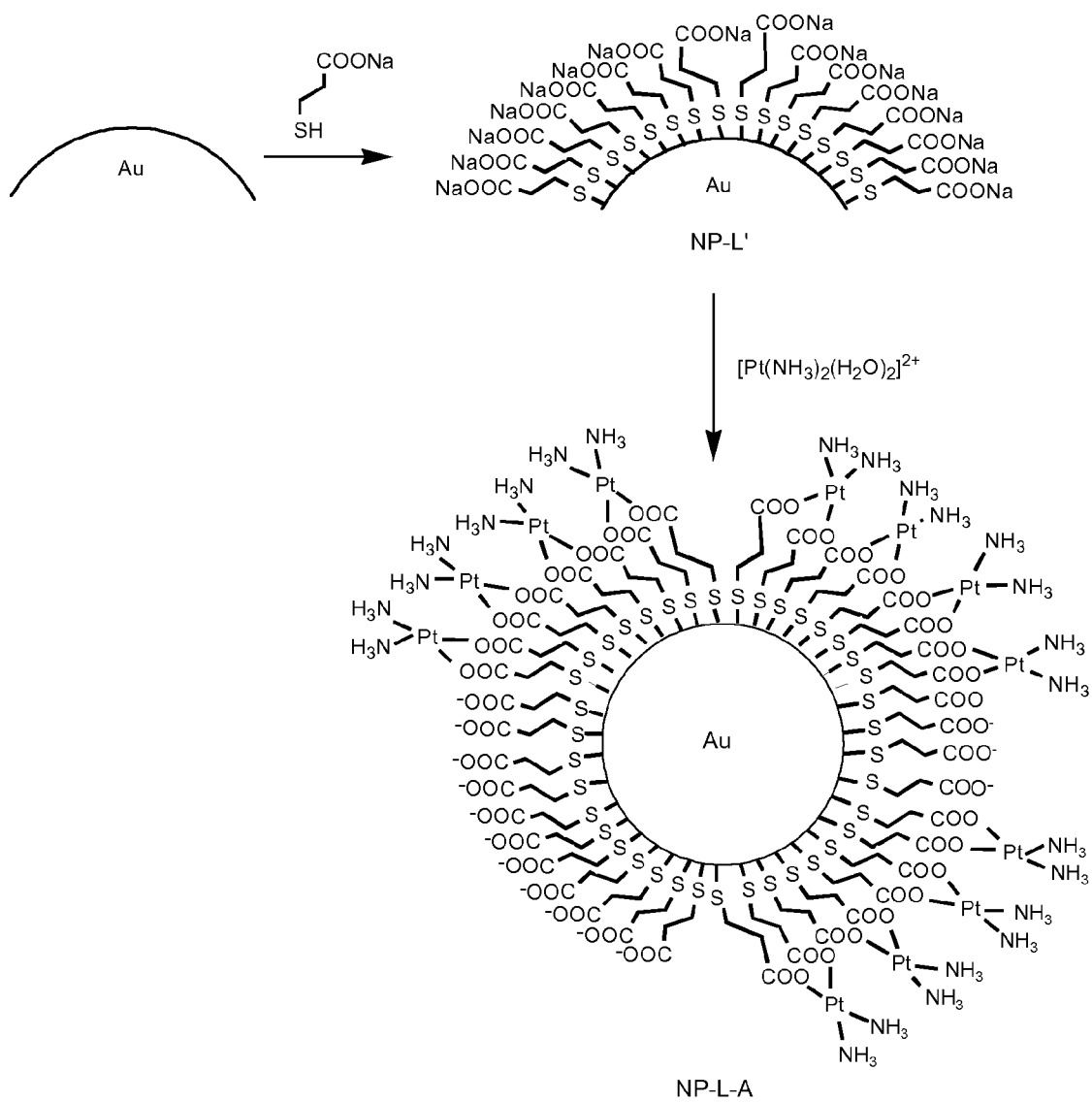
FIG. 1 shows a schematic view of a conjugate according to the invention, in particular a conjugate of formula (I) NP-L-A, wherein NP is a gold nanosphere; L corresponds to mercaptopropanoic acid (MPA); and A is a platinum (II) biradical obtained from cisplatin.

A schematic view of a conjugate of formula (I) NP-L-A, wherein NP is a gold nanosphere; L is a linker of formula (II) wherein X represents —(CH$_2$)$_m$—, n=0 and m=2; and A is a platinum (II) biradical of formula (IV) is shown in FIG. 1.

As mentioned above, the conjugates of formula (I) may be conveniently prepared by a two-step process, firstly by preparing an intermediate conjugate NP-L' and secondly, attaching the platinum containing compound to this intermediate conjugate.

In the first step of the process, an excess of a compound of formula (IIa) or formula (IIIa), or a stereoisomer or a salt of any of these formulas, in an aqueous solution is used in order to give rise to the intermediate conjugate of formula NP-L' as defined above, wherein L' is a linker of formula (IIb) or formula (IIIb)

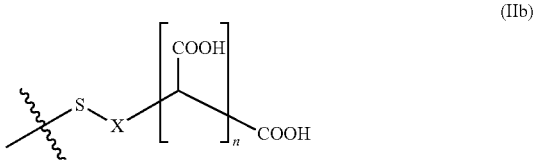

(IIb)

Generally, it is assumed that this reaction in the presence of an excess of a compound of formula (IIa) or formula (IIIa), or a stereoisomer or a salt of any of these formulas, leads to an intermediate conjugate NP-L', wherein the whole surface is coated with the linker L'.

In a preferred embodiment, a compound of formula (IIa) is used, which is 11-mercaptoundecanoic acid (MUA) or 3-mercaptopropanoic acid (MPA). In another preferred embodiment, a compound of formula (IIIa) is used which is 5-[(3R)-dithiolan-3-yl]pentanoic acid (also named as alpha lipoic acid or thioctic acid).

Small nanoparticles are difficult to purify by centrifugation, therefore the non-reactive molecules of the compound of formula (IIa) or formula (IIIa) and the reducing agent may be eliminated via dialysis of the colloidal solution present in solution after conjugation.

The uncoated metallic nanoparticles may be prepared by using synthesis protocols for nanoparticles that allow the simple and scalable production of monodisperse nanoparticles with control of size and shape. In particular, the nanoparticles may be prepared by rapid injection of a metallic salt selected from a salt of Au, Ag and Pt in a reducing agent, thus producing a temporally discrete homogeneous nucleation employed for the production of monodisperse metallic nanoparticles. The reducing agent may be, for example, citrate at high temperature (classical Turkevitch method), sodium borohydride or a mixture of sodium borohydride and ascorbic acid, optionally in the presence of Cetyl Trimethyl Ammonium Bromide (CTAB).

The formation of metallic nanoparticles may be observed by a change in colour in the reaction medium. Depending on the method used the nanoparticles obtained will have a different size and shape in the presence of the right surfactants as CTAB.

In a second step, the intermediate conjugates of formula NP-L' are further reacted with a platinum compound selected from the group consisting of formula (IVa), formula (Va) and formula (VIa), including the stereoisomers of all of them,

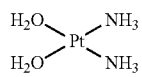
(IVa)

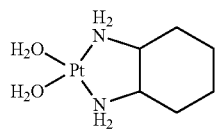
(Va)

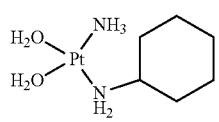
(VIa)

to give rise to a conjugate of formula (I), wherein A is a platinum (II) biradical selected from the group consisting of formula (IV), formula (V) and formula (VI) respectively, wherein the biradical of formulas (IV), (V) and (VI) is optionally in form of a salt. This reaction may be carried out in an aqueous solution in the presence of a base in order to deprotonate the carboxylic acid groups of the linker L' of formula (IIb) or formula (IIIb).

The compounds (IVa), (Va) and (VIa), including the stereoisomers of all of them, may form a salt in the presence of an anion such as, for example, chloride or nitrate.

As mentioned above, in order to obtain a soluble conjugate of formula (I), that is a conjugate having colloidal stability in the medium, some charge has to be maintained at the surface to provide the NPs with enough electrostatic charge and repulsion to avoid aggregation and precipitation. Thus, the surface is coated with linker molecules ending in carboxyl groups (COO), which at physiological pH are deprotonated and present negative surface charge. Then, platinum drug molecules are linked to a fraction of the carboxyl terminations, so that some of the surface charge is cancelled, but leave enough charge for the electrostatic repulsion.

In order to reach the desired degree of drug loading (i.e. the highest possible therapeutic effects while preserving enough surface charge to avoid destabilization and aggregation) two different approaches can be followed: a) a previously calculated amount of platinum compound, which complies with the above requirements, can be mixed with the NP-L' intermediate conjugates, or alternatively b) an excess of platinum compound can be mixed with the NP-L' intermediate conjugates.

In the first case, the amount of the platinum (II) compound has to be previously calculated. This amount may be easily determined by routine tasks. In particular, a calibration curve using different amounts of platinum (II) compound may be used. The idea behind this is that different amounts of platinum (II) compounds are reacted with the intermediate conjugates and the resulting conjugates are analysed by UV-Vis spectroscopy. When the amount of platinum compound is too high to lead to a conjugate having colloidal stability, and thus, an aggregate is formed, this can be detected by the red-shift of the UV-Vis peak when comparing the UV-Vis spectra of the resulting conjugate and the corresponding intermediate conjugate. Thus, the amount of platinum compound is subsequently reduced until no aggregation is observed.

Figure 3:
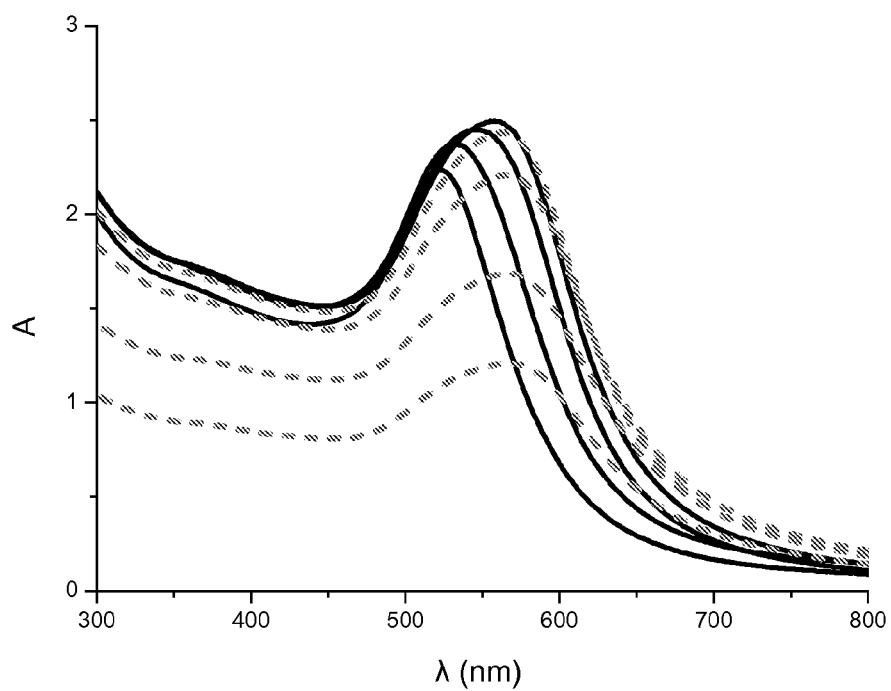
FIG. 3 shows the temporal evolution of cisplatin attachment to linker-coated nanoparticles.

In the second case, when an excess of platinum compound is used, the conjugation is stopped before too many platinum compound molecules are attached to the linker molecules. The inventors have found that, when monitoring the attachment of the platinum compound to linker coated nanoparticles, if the process is not efficiently stopped, the platinum compound continues coating the linker layer and the nanoparticles become unstable. FIG. 3 shows the UV-Vis spectroscopy analysis of reaction aliquots taken every ten minutes (NP: 20 nm gold nanosphere, L: 11-mercaptoundecanoic acid (MUA), A: cisplatin). In black lines are represented the initial stage. Stability of nanoparticles is maintained in this stage, although it can be observed the presence of some agglomerates in the later times. In dashed lines are shown the final stages when the aggregation of the particles due to the loss of stability (cisplatin quenches the stability given by MUA layer) leads to precipitation of the nanoparticles.

Therefore, when working with an excess of platinum compound, the attachment of platinum compound molecules to the linker molecules has to be stopped when the charge of platinum drug is maximal and the resulting conjugate is still stable. This cannot be achieved spontaneously. To stop the conjugation the conjugating solution is placed for example in a dyalisis bag where from the free platinum compound molecules escape rapidly leaving the conjugate NP-L' partially coated with the platinum compound. The time at which the reaction has to be stopped can be previously calculated in experiments similar to the one shown in FIG. 3. This last procedure has the advantage that it is faster and more controlled.

Conjugation may be monitored by the combination of series of experiments including dynamic light scattering (DLS), UV-Vis spectroscopy, Zeta Potential, transmission electron microscopy (TEM), optical microscopy, Gel Electrophoresis and ICP-MS for quantitative analysis.

The compound of formula (IVa) may be synthesized starting from the compound of formula (VII) (cisplatin) or formula (VIII) (carboplatin); the compound of formula (Va) may be synthesized starting from the compound of formula (IX) (oxaliplatin); and the compound of formula (VIa) may be synthesized starting from the compound of formula (X).

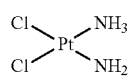
(VII)

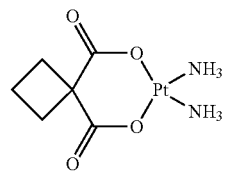
(VIII)

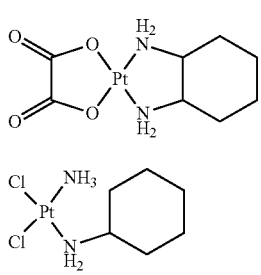

(IX)

(X)

In the case of cisplatin, the conversion is carried out by treating the compound with a source of a Ag cation, such as AgNO$_3$, to remove Cl from the cisplatin molecule and yield the hydrated species. In the case of carboplatin, the compound is converted to a compound of formula (IVa) by hydrolysis of the COO bonds by standard methods well-known in the art. Similarly, a compound of formula (VII) may be converted to a compound of formula (V) by analog methods.

Alternatively, the compounds of formula (Va) and (VIa) may be obtained by a two-step synthesis comprising: 1) reacting PtCl$_4$ with the corresponding amine: cyclohexane-1,2-diamine or ammoniac/cyclohexylamine to yield intermediates (Vb) and (VIb), and

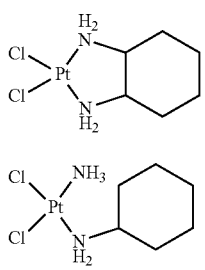

(Vb)

(VIb)

2) treating the intermediates obtained in step 1) with a source of a Ag cation, such as AgNO$_3$, to remove Cl and yield the hydrated species (Va) and (VIa) respectively.

The undesired side-products, in particular, trans platinum compounds, may be removed by means of chromatography.

The fact that a platinum compound of formula (IVa), (Va) or (VIa) is conjugated to the intermediate conjugate NP-L' instead of the platinum compounds of formulas (VII) to (X) has important consequences. Thus, in the conjugates of the invention, coordination bonds between the linker and the platinum compound are formed. These bonds, as already mentioned are strong and provide for stability of the molecule, in particular in a medium at physiological conditions. These bonds are only hydrolyzed at low pH, such as the one present in the in endosomes and endolysosomes.

On the other hand, when cisplatin is directly conjugated to an intermediate conjugate of formula NP-L' as it has been described in the prior art, electrostatic bonds between the linker and the platinum compound are formed. Generally, electrostatic bonds are not so strong as coordination bonds (about 0.4 Kcal/mol in aqueous solution with electrolytes). In particular, these bonds, as opposed to the conjugates of the invention, lead to conjugates which show colloidal instability (aggregation and precipitation). This will be shown in more detail in the examples.

The pharmaceutical compositions of the invention may be formulated as solid or liquid compositions. In a preferred embodiment, the administration of the pharmaceutical composition is intramuscular, intravenous, intraperitoneal or intratumoral. Generally, suitable formulations include aqueous and non-aqueous, isotonic sterile injection solutions which have suitable pH and stability, which can contain for instance anti-oxidant agents, buffers and bacteriostatic agents; and aqueous and non-aqueous sterile suspensions that may include suspending agents, solubilizers, thickening agents, stabilizers, and preservatives.

As already mentioned the conjugates of the invention may be useful for the treatment of cancer in a patient suffering therefrom, especially in cases where surgery is not feasible.

Representative cancers of interest include, but are not limited to head, neck and lung tissue; gastrointestinal tract and pancreas, such as gastric carcinoma, colorectal adenoma, colorectal carcinoma and pancreatic carcinoma; hepatic tissue, such as hepatocellular carcinoma; Kidney and urinary tract, such as bladder carcinoma, renal carcinoma; breast tissue, such as breast carcinoma; neural tissue, such as neuroblastoma and meningioma malignant; skin tissue, such as melanoma; and hematological tissues, such as lymphoma and leukemia.

Those of skill in the art will readily appreciate that dose levels may vary, among others, as a function of the specific compound, the nature of the delivery vehicle, and the nature of the tumor to be treated. In a particular embodiment, in order to have realistic doses for the in vivo application of the invention, the concentration of the conjugates is increased about 50 times. To this end, the nanoparticles are precipitated by centrifugation and the pellet recovered and re-dissolved in progressively decreasing amounts of solvent without loosing any stability.

The conjugates of the invention have the advantage that they reduce the side effects in comparison with the currently used therapies with cisplatin and analogs.

The conjugates of the invention may concentrate on the tumors as a result of the Enhanced Permeability and Retention effect (EPR). Briefly, the EPR effect, is the result of defective tissue integrity, changes in permeation mediators and impaired lymphatic drainage in tumors. Thus, the vascular endothelium of tumors tends to have relatively large gaps that allow larger molecular species up to 200 nm to permeate the tissue rather than in healthy tissues. The altered permeation mediators and impaired lymphatic drainage mechanism then assure that the molecules that have penetrated the tumor stay there. Thus, the conjugates of the invention passively accumulate in the tumor and from there are internalized via endocytosis. An advantage of this id that lower quantities of platinum drug need to be administered with results in less side-effects.

Moreover, due to the conjugation, the conjugates are inactive in the systemic circulation and they are only activable after reaching tumour, or in the liver, as particulate matter does, where no toxicity has been observed. When entering the tumoral cell, once in the endosome, the low pH used by the digestive apparatus of the cell (the endolysosome, resulting from the fusion of the endosome and the lysosome) leads to the hydrolysis of the coordination bond between the linker and the platinum drug, so that the platinum drug is released close to the nucleous.

As already mentioned, the invention also relates to a method for the treatment of cancer comprising administering to a mammal in need thereof, including a human, a therapeutically effective amount of a conjugate of formula (I) together with one or more pharmaceutically acceptable excipients. In a particular embodiment, the later method further comprises locally irradiating the tumor with radiotherapy at any frequency (from gamma to XR, NIR and MW) in order that the platinum drug becomes more effective.

EXAMPLES

The following examples are provided for illustrative means, and are not meant to be limiting of the present invention.

Characterization Techniques

1) UV-Vis Spectroscopy

UV-Visible spectra were acquired with a Shimadzu UV-2400 spectrophotometer. 1 mL of nanoparticles or conjugates were placed in a cell, and spectral analysis was performed in the 300 nm to 800 nm range.

2) Zeta Potential

The zeta potential of nanoparticles and conjugates was determined using a Malvern ZetaSizer Analyzer (Malvern Instruments, UK). These measurements were performed with control of the pH (7.0).

3) X-Ray Photoelectron Spectroscopy (XPS)

For XPS, 10 μL of a solution of nanoparticles or conjugates was placed on a silicon nitride surface and analysed using PHI ESCA-5500 equipment. A monochromatic Al K_Xray source was used and the chamber was maintained below $2 \times 10^{-9}$ Torr. Spectra were analysed using Multipak software.

Example 1

Synthesis of Gold Nanospheres (AuNP)

Example 1.1

Gold Nanospheres Having a Diameter of 4 nm

Ice-cold freshly prepared aqueous solution of NaBH$_4$ (0.1 M, 0.6 mL) was added to 20 mL aqueous solution of HAuCl$_4$ (0.25 mM) and trisodium citrate (0.25 mM) while stirring at room temperature. The solution turned pink immediately after addition of NaBH$_4$, indicating particle formation. Following this method gold nanospheres having a diameter of 4 nm were obtained.

Figure 4:
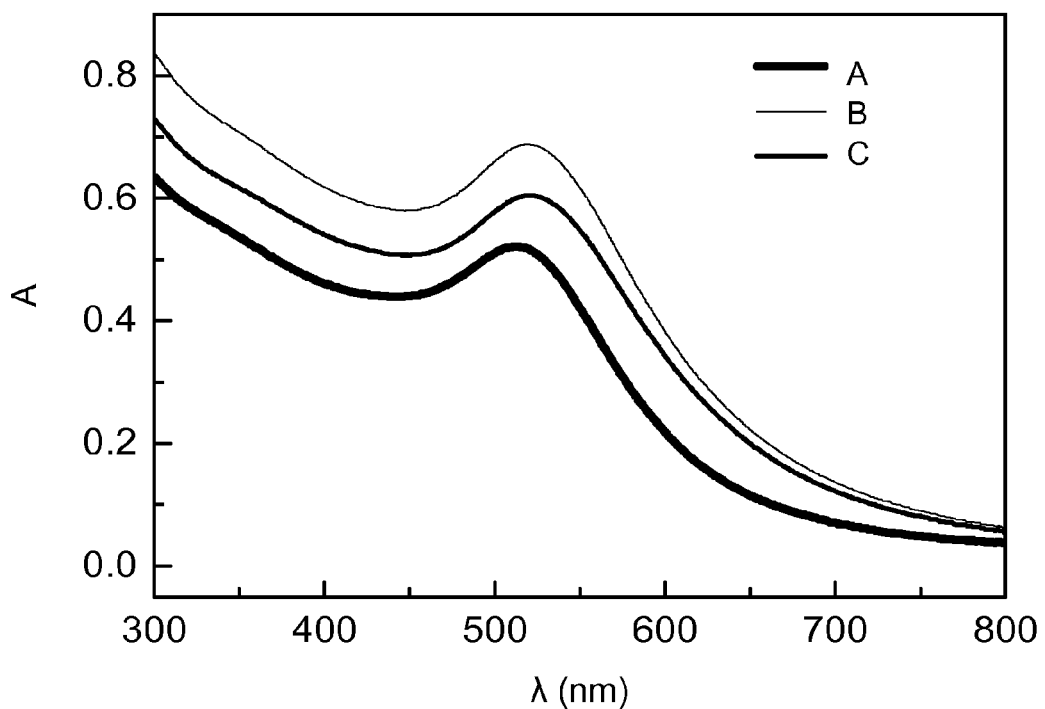
FIG. 4 shows UV-Vis spectra (absorbance versus wavelength) monitoring the red-shift of the surface plasmon resonance (SPR) band due to conjugation. A represents uncoated gold nanospheres of example 1.1; B represents the intermediate conjugate of example 2.1; and C represents the conjugate of example 4.1.
Figure 5:
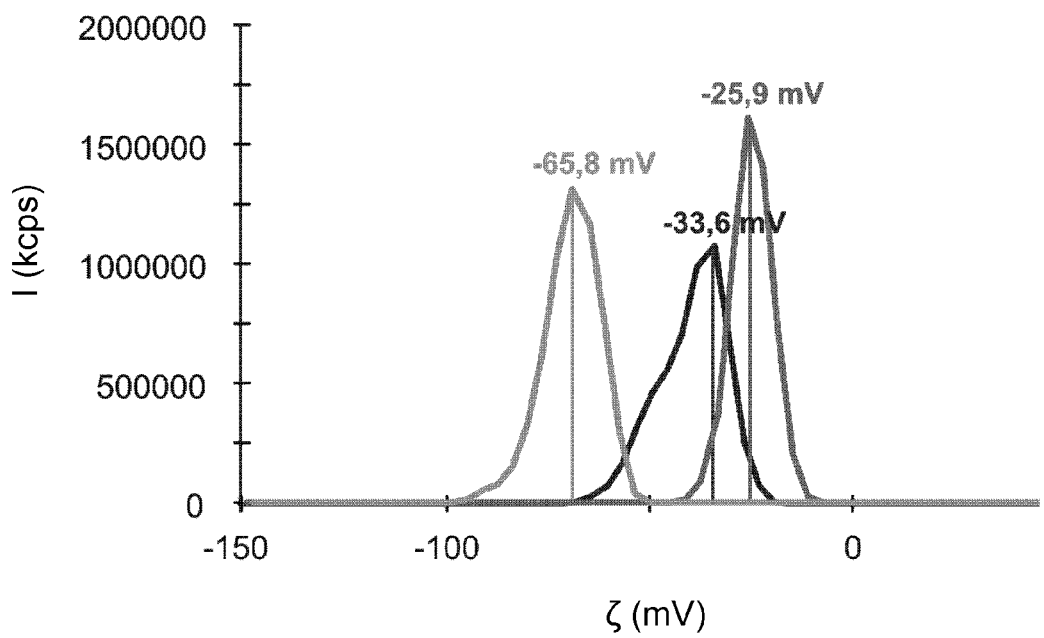
FIG. 5 shows the ζ-potential drop as the nanoparticle surface is coated (intensity versus Zeta potential). The Zeta potential of −25.9 mV corresponds to the conjugate of example 4.1; the Zeta potential of −65.8 mV corresponds to the intermediate conjugate of example 2.1; and the Zeta potential of −33.6 mV corresponds to the uncoated gold nanospheres of example 1.1.
Figure 6A:
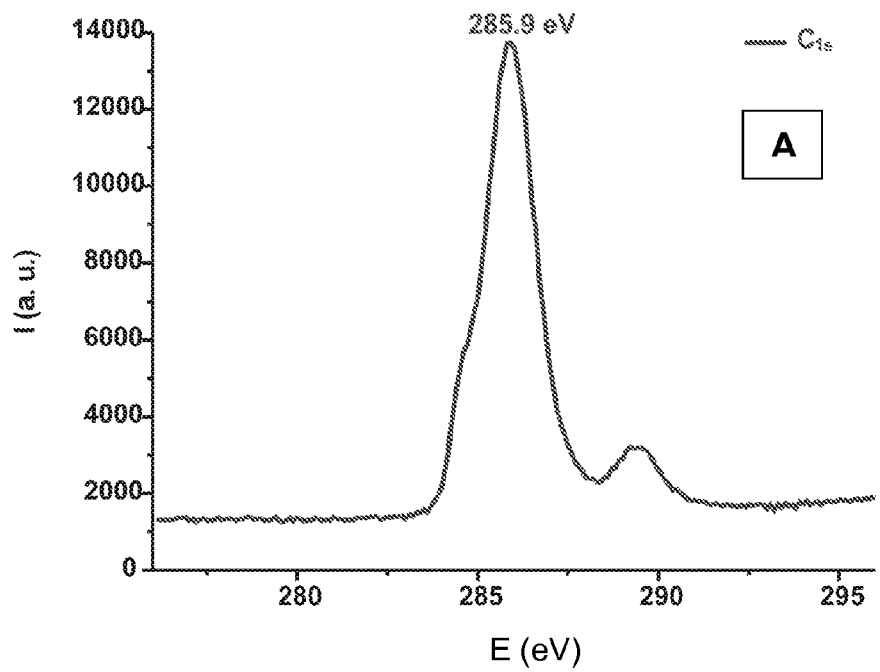
FIG. 6, which includes and is defined by sub-part FIGS. 6A, 6B, 6C and 6D.
Figure 6B:
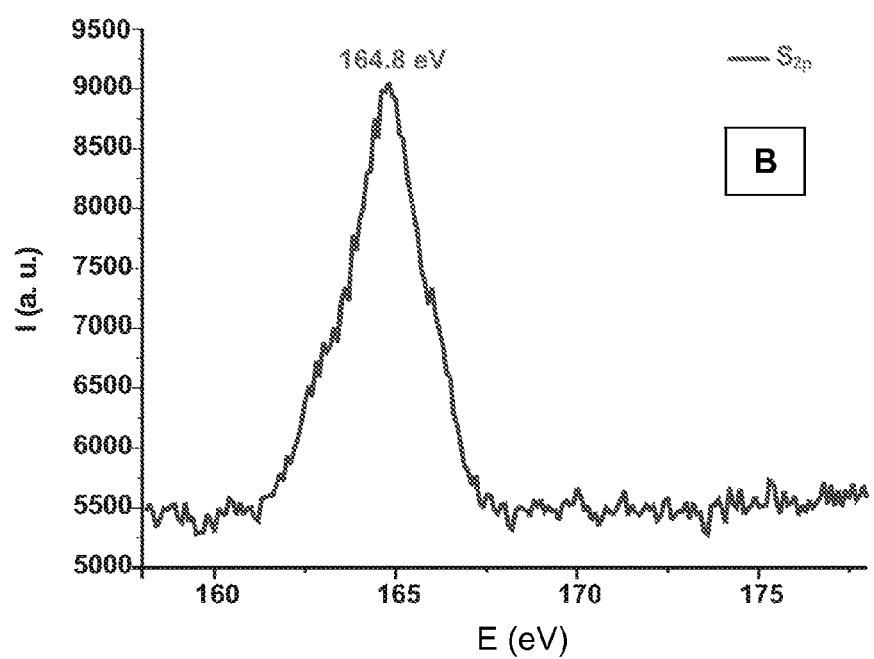
Figure 6C:
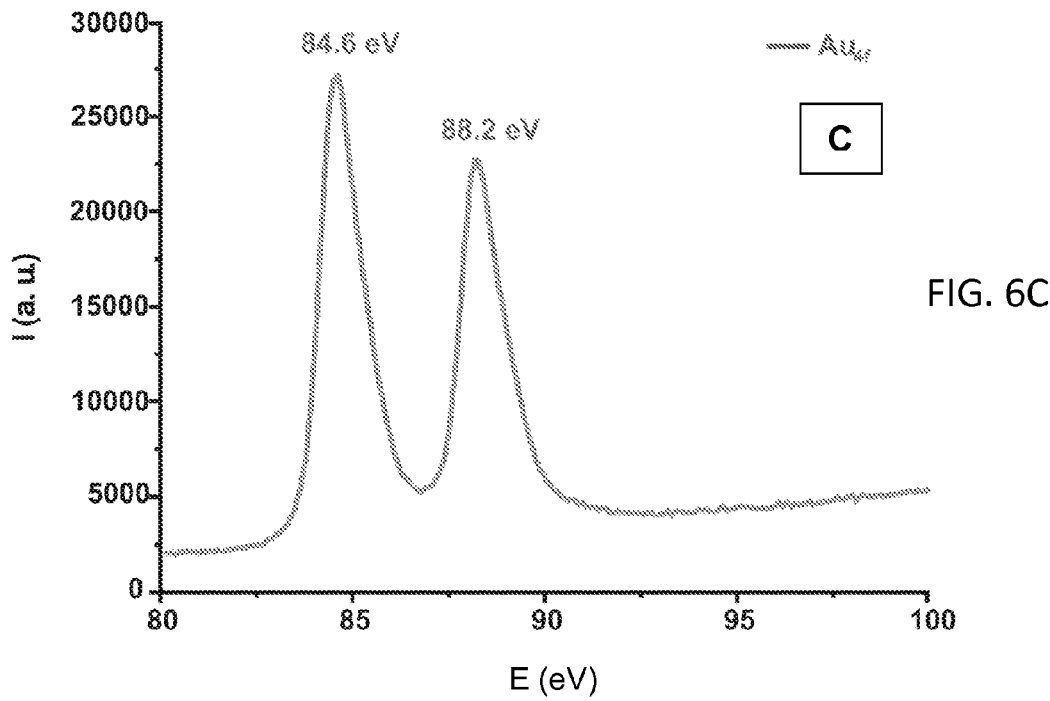
Figure 6D:
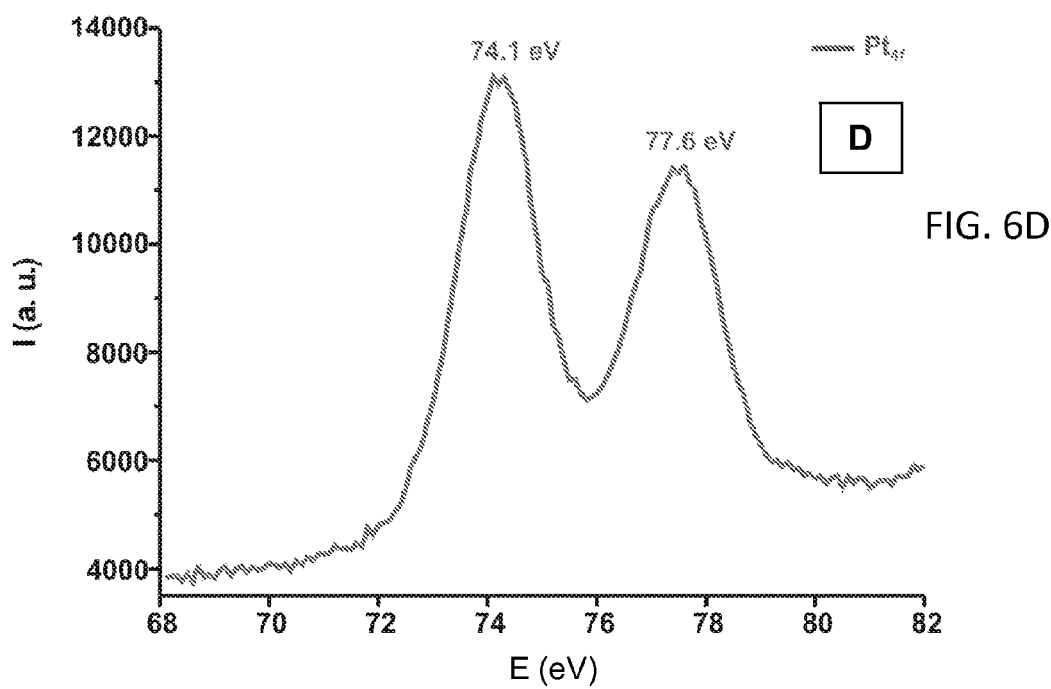

Characterization of the colloidal solution was carried out by UV-Vis spectroscopy obtaining a $\lambda_{max}$=512.5 nm (FIG. 4, A) and ζ-potential (−33.6 mV, FIG. 5, A).

Following a similar procedure (Turkevich Method), the following nanoparticles were obtained:

Example 1.2

Figure 7:
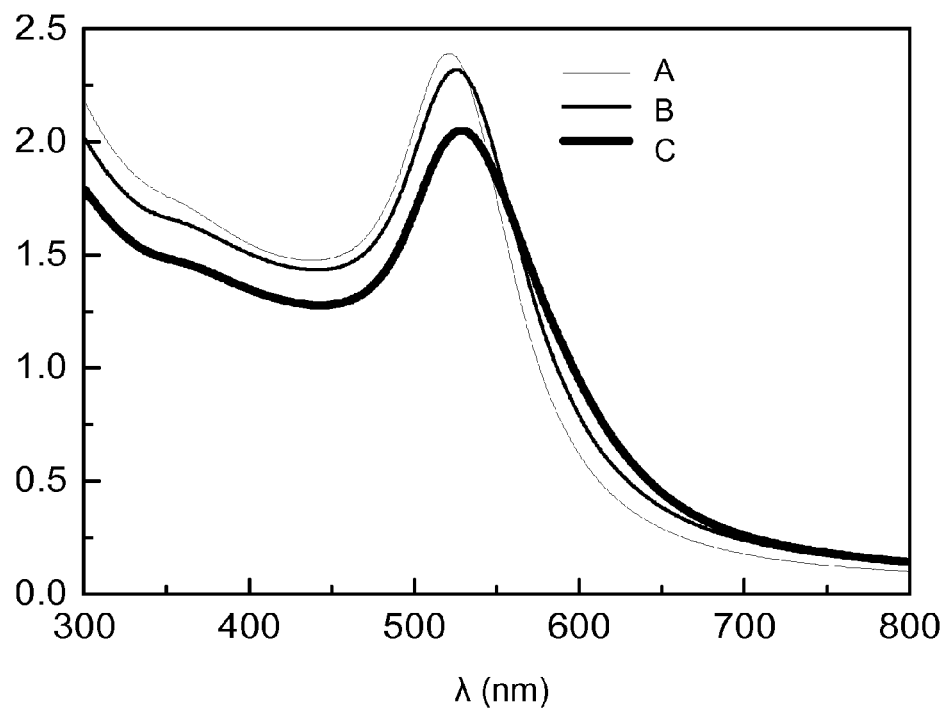
FIG. 7 shows UV-Vis spectra (Absorbance versus Wavelength) monitoring the red-shift of the surface plasmon resonance (SPR) band due to conjugation. A represents uncoated gold nanospheres of example 1.2; B represents the intermediate conjugate of example 2.2; and C represents the conjugate of example 4.2.

Gold Nanospheres Having a Diameter of 13 nm (FIG. 7, A)

Example 1.3

Figure 8:
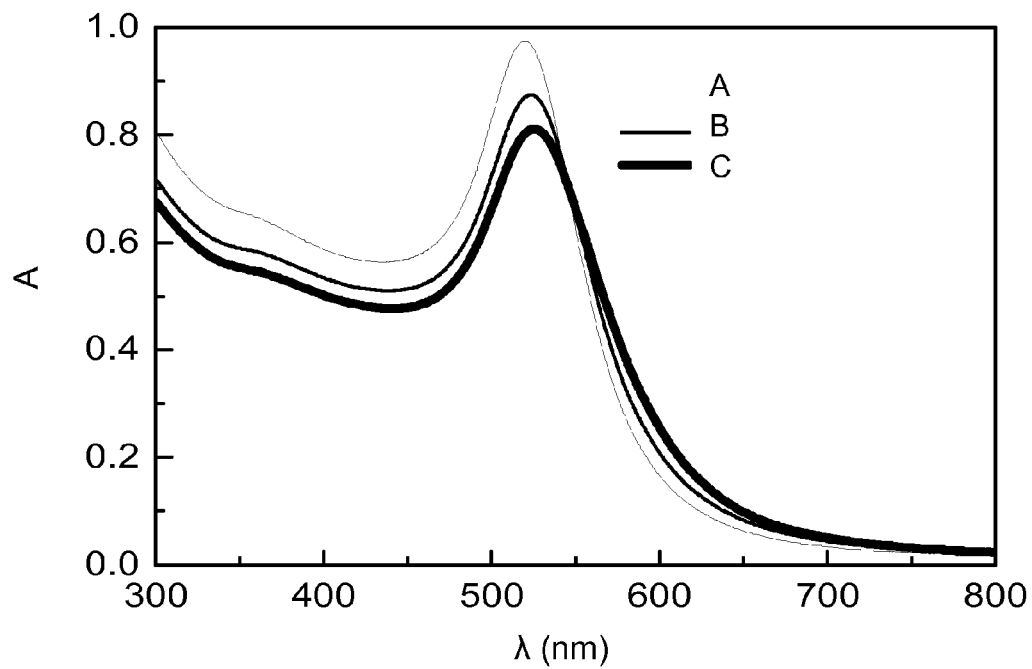
FIG. 8 shows UV-Vis spectra (Absorbance versus Wavelength) monitoring the red-shift of the surface plasmon resonance (SPR) band due to conjugation. A represents uncoated gold nanospheres of example 1.3; B represents the intermediate conjugate of example 2.3; and C represents the conjugate of example 4.3.

Gold Nanospheres Having a Diameter of 20 nm (FIG. 8, A)

Example 2

Intermediate Conjugates (AuNP-L')

Example 2.1

Intermediate Conjugates AuNP(NP:13 nm)-MUA

The conjugation was carried out by addition of an aqueous solution of mercaptoundecanoic acid (MUA, 10 mM, 50 μL/mL NPs), to the AuNP solution obtained in example 1.1). The reaction took place at room temperature, observing an instantaneously color change of the colloidal solution upon addition of the thiolated molecules. The reaction was allowed to run for at least 30 min to reach optimal conjugation. Purification was done by dialysis against MilliQ H$_2$O (10 mL of NPs/5 L of H$_2$O) at neutral pH for two days. AuNP(NP: 4 nm)-MUA intermediate conjugates were characterized by UV-Vis spectroscopy ($\lambda_{max}$=519 nm, FIG. 4, B), ζ-potential (−65.8 mV, FIG. 5, B) and XPS confirming the conjugation step ($S_{2p}$ 164.8 eV).

Following the same procedure as described above, the following intermediate conjugates were obtained:

Example 2.2

AuNP(NP:13 nm)-MUA Intermediate Conjugates (FIG. 7, B). Example 2.3: AuNP(NP:20 nm)-MUA Intermediate Conjugates (FIG. 8, B).

Similarly, following the same procedure as described above, but using thioctic acid (TA) instead of MUA, the following intermediate conjugate was obtained:

Example 2.4

Figure 9:
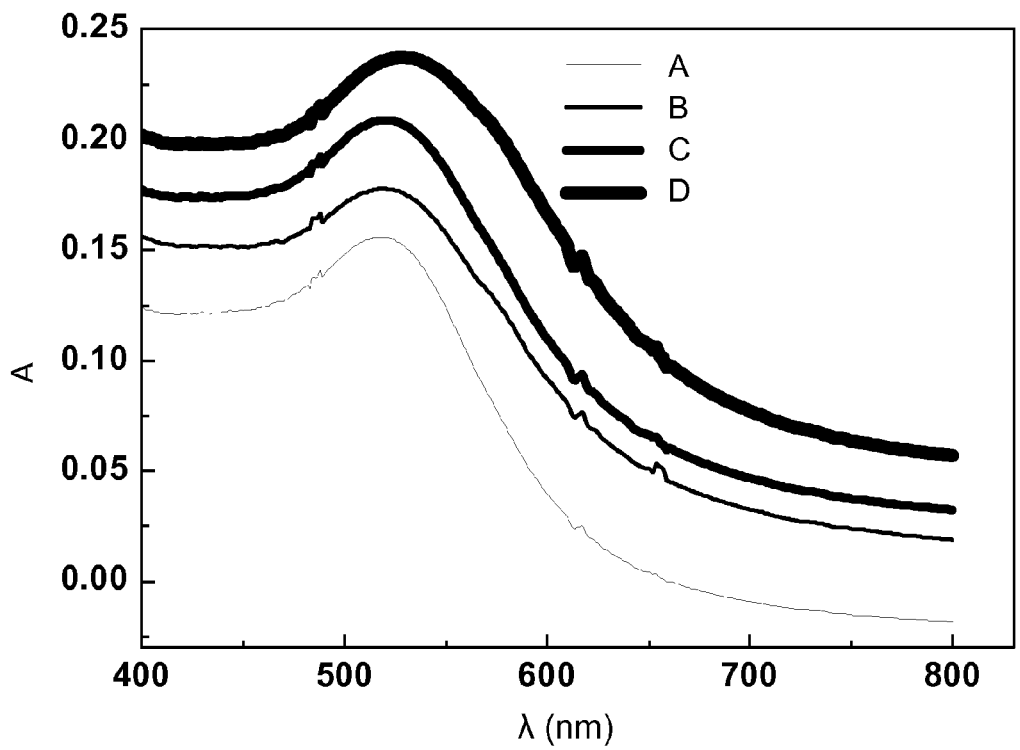
FIG. 9 shows UV-Vis spectra (Absorbance versus Wavelength) monitoring the red-shift of the surface plasmon resonance (SPR) band due to conjugation. A represents uncoated gold nanospheres of example 1.4; B represents the intermediate conjugate of example 2.4; and C represents the conjugate of example 4.4 at a 5 μM platinum concentration; and D represents the conjugate of example 4.4 at a 50 μM platinum concentration.

AuNP(NP:4 nm)-TA Intermediate Conjugate (FIG. 9, B)

Example 3

Synthesis of Platinum Derivatives: cis-[Pt(NH$_3$)$_2$(H$_2$O)$_2$](NO$_3$)$_2$ (Compound of Formula (IVa))

A solution of AgNO$_3$ (169 mg, 1 mmol) in 2.5 mL H$_2$O was added dropwise to a suspension of cisplatin (150 mg, 0.5 mmol) in 2.5 mL H$_2$O. A white solid (AgCl) precipitates and the yellow color of the initial mixture vanishes after completing the addition. The resulting suspension was heated to 50° C. for 1 h and AgCl was then separated by centrifugation. The supernatant solution was evaporated to dryness and the residue recrystallised from an ethanol/water mixture. Yield: 174 mg (89%).

Example 4

Synthesis of Conjugates AuNP-L-A

Example 4.1

AuNP(NP:4 nm)-MUA-Pt Conjugates

A colloidal solution of example 2.1 (10 mL, ≈7.12×10$^{13}$ NP/mL) was brought to basic pH (9-14) with an aqueous solution of NaOH (0.1 M). An excess of the compound of formula (IVa) obtained in step 3 (0.5 equiv. respect to the excess of MUA added) was added to the solution while stirring at room temperature. The reaction was allowed to run for at least 30 min. and purification was carried out via dialysis of the conjugated colloidal solution (5 mL AuNP(NP:4 nm)-MUA-Pt conjugates/5 L MilliQ H$_2$O) at neutral pH for 2 days. Characterization was done by UV-Vis spectroscopy observing a red shift in the surface plasmon resonance of 1.5 nm ($\lambda_{max}$=520.5 nm). In addition, characterization by XPS confirms the presence of Pt derivatives on the nanoparticles (Pt$_{4f}$ 74.1 and 77.6 eV). Quantification of the drug on the AuNP solution was measured by ICP-MS (1.9 mg/L).

The obtained conjugates were characterized by UV-Vis spectroscopy (FIG. 4, C), ζ-potential (−25.9 mV, FIG. 5) and XPS confirming the conjugation step (FIG. 6).

Following the same procedure as described above, but starting from intermediate conjugates of examples 2.2, 2.3 and 2.4, the following conjugates were obtained respectively:

Example 4.2

AuNP(NP:13 nm)-MUA-Pt (FIG. 7, C)

Example 4.3

AuNP(NP:20 nm)-MUA-Pt (FIG. 8, C)

Example 4.4

AuNP(NP:4 nm)-TA-Pt (FIG. 9, C and D)

Example 5

Synthesis of a Conjugate AuNP(NP:4 nm)-MUA-cisplatin (Comparative Example)

This example was aimed at comparing effect of conjugates obtained via electrostatic interactions. For this purpose an intermediate conjugate AuNP-MUA, wherein the nanospheres have a diameter of 4 nm as obtained in step 2 was further functionalized with cisplatin as follows:

Conjugates AuNP-MUA (example 2.1, 5 mL of $10^{12}$ NP/mL) were dispersed in 5 mL of a 1 mg/mL of aqueous commercial cisplatin solution after at least three washes. The absorption of cisplatin on the coated nanoparticles was allowed to take place over 2 days. Excess of cisplatin was removed by centrifugation. The drug loaded conjugates were washed at least three times and dispersed in water.

Figure 10:
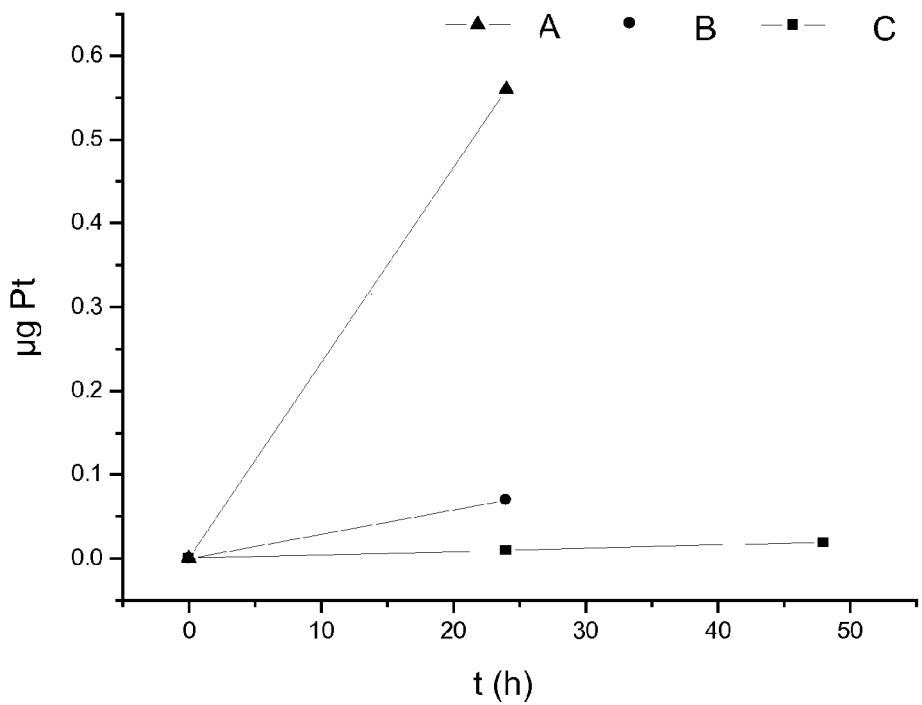
FIG. 10 shows stability measured as the variation in time of the amount of atomic platinum of A: the conjugate of example 4.1 in cell media; B: the conjugate of example 5 in water; and C: the conjugate of example 5 in cell media.

The stability of these conjugates was compared with the stability of the conjugates of the invention. FIG. 10 shows stability measured as the variation in time of the amount of atomic platinum of A: the conjugate of example 4.1 in cell media; B: the conjugate of example 5 in water; and C: the conjugate of example 5 in cell media. After 48 h of incubation with cellular medium at 37° C., release of platinum drug from the nanoparticle was only observed in the case of conjugates formed via electrostatic interactions. The stability tests were based on inductively coupled plasma mass spectroscopy ICP-MS quantifications of platinum drug release after incubation of both systems.

MTT Assay of the Conjugates in Tumoral Cells

Cells were plated in a multiwell-96 plate (Iwaki) at $4 \times 10^3$ cells/well and 24 hours later the medium was changed for treatments. Tetrazolium salt 3-(4,5-dimethylthiazol-2-yl)-2,5-diphenyltetrazoliumbromide (MTT, Acros Organics) was used for mitochondrial activity evaluation in cell viability studies 24 and 48 hours post-treatments. Plates were measured in MicroPlate Reader Model 550 (BIO-RAD) and data were processed with Excel and SPSS software. Using absorbance measurements [time zero, (Az), control growth, (C), and test growth in the presence of drug at the various concentration levels (Ai)], the percentage growth was calculated at each of the drug concentration levels. The assays were done with three cellular cancer lines: HeLa, A549 and HEK. Studies with the different cultured cancer cells (HeLa, A549 and HEK) showed that the conjugates of the invention, in particular the conjugates of example 4.1, achieved higher intracellular drug levels than when free cisplatin was administered to these cells.

Figure 11:
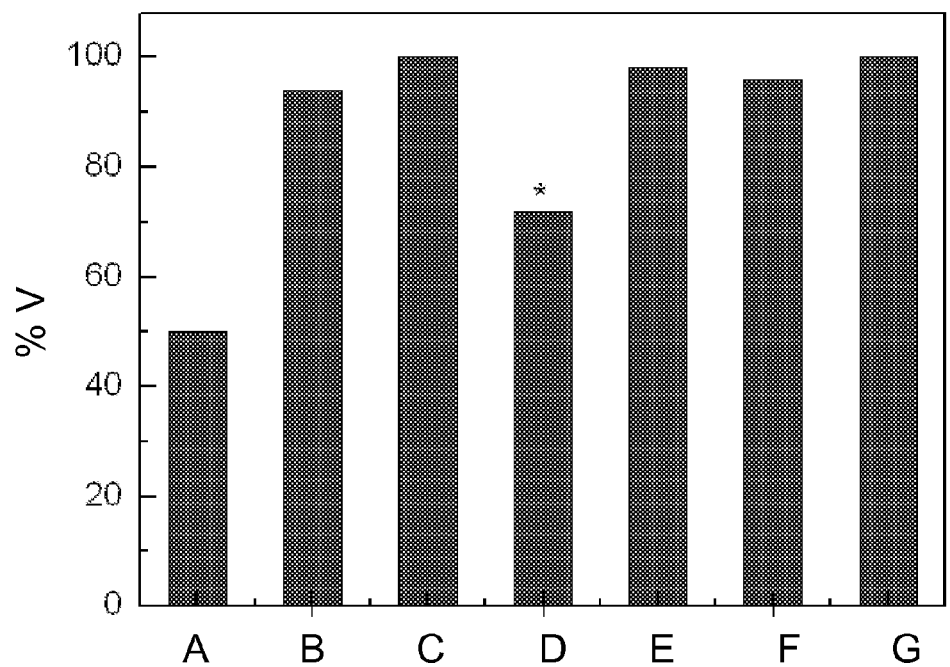
FIG. 11 shows a MTT assay of the effect of the conjugates in the viability of the A549 tumor cells (a human lung carcinoma derived cell line). B represents the uncoated gold nanospheres of example 1.1; C represents the intermediate conjugate of example 2.1; D corresponds to the conjugate of example 4.1; E corresponds to commercial cisplatin; F corresponds to the cisplatin derivative of example 3; and A and G represent the control values at 0 and 48 h respectively.

FIG. 11 shows the % of A549 lung tumoral cells viability when exposing the cells to the uncoated gold nanospheres of example 1.1 (B); to the intermediate conjugate of example 2.1 (C); to the conjugate of example 4.1 (D); to commercial cisplatin (E); and to the cisplatin derivative of example 3 (F). A and G represent the control values at 0 and 48 h respectively. As it can be seen a significant proliferation arrest was observed when exposing the cells to the conjugate of the invention (D), showing the cytostatic effect of the conjugate. On the contrary, uncoated nanoparticles, intermediate conjugates, or hydrated cisplatin derivative did not elicit any response.

Animal Assay

Figure 12:
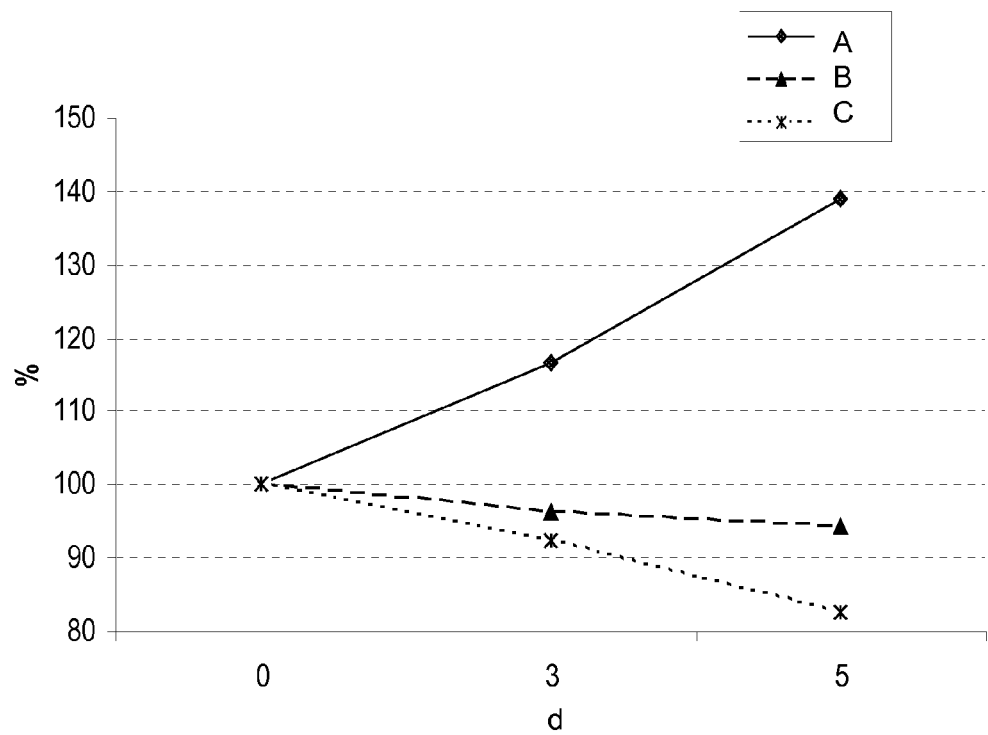
FIG. 12 shows the % of tumor size increase in time (days) for three different groups: A corresponds to the non-treated group; B corresponds to the group treated with commercial cisplatin; and C corresponds to the group treated with the conjugates of example 4.1.

Fifteen SCID mice were choosen for the in vivo experiment. Mouse were injected 20 106 A549 lung tumoral cells in their flanks. Three random groups of five mice each were prepared. Then we waited until the tumour grew to an easily measurable size. The first group (A) was given no treatment. The second group (B) was given mild doses of commercial cisplatin (30 mg per Kg animal weight). The third group (C) was treated with the conjugates of example 4.1 with 100 ml of 1.9 mg of platinum drug per litre in one intra-peritoneal dose. Tumour size (as a sign of therapeutical success) and animal weight (as a sign of secondary effects) were measured every three days. After fifteen days the experiments were stopped. As shown in FIG. 12, in the first case (A) the tumour growth as expected. In the second case (B), there was a reduction of tumour size, as expected, and a loose of body weight (not shown), as a secondary effect of the treatment. In the third case (C), a larger tumour reduction was observed at doses 5 times lower than the free cisplatin, and no body weight loose was observed (not shown), consistent with the lower dose or the modified biodistribution of the platinum drug attached to the nanoparticle or both. Preliminary biochemical measurements did not indicate any kidney and hepatic significant dysfunction in any case, what is consistent with the low doses used in each case.

The invention claimed is:
1. A conjugate of the formula (I)

NP-L-A    (I)

having colloidal stability in a medium wherein
NP is a gold, silver or platinum nanoparticle;
L is a linker of formula (II) or a stereoisomer thereof, which is attached to the nanoparticle NP through the sulfur atom; or L is a linker of formula (III) or a stereoisomer thereof, which is attached to the nanoparticle NP through the two sulfur atoms

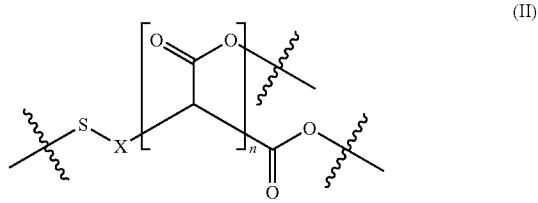

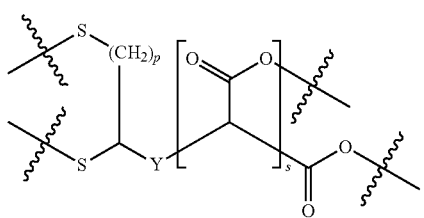
(III)

wherein:
X and Y independently represent a $(C_2$-$C_{20})$hydrocarbon chain, wherein at least one carbon atom is optionally replaced by a CO group or a heteroatom selected from the group consisting of O and N; and wherein the $(C_2$-$C_{20})$hydrocarbon chain is optionally substituted with one or more substitutents selected from the group consisting of halogen, OH, $CONH_2$, $CO_2(C_1$-$C_6)$alkyl and —CHO;
n and s independently represent a value from 0 to 1;
p represents a value from 1 to 2; and
A is a platinum (II) biradical selected from the group consisting of formula (IV), formula (V) and formula (VI) including any of the stereoisomers of all of them, wherein the biradical is optionally in the form of a salt, and is attached to the linker L through the single bonded oxygen atom of the carboxyl groups

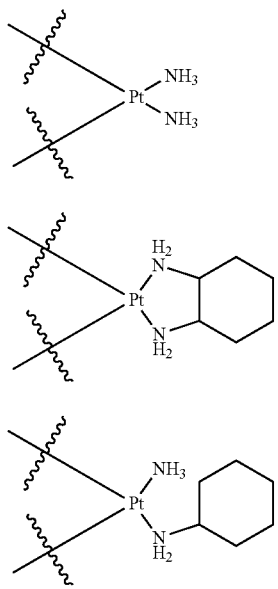

(IV)

(V)

(VI)

with the condition that:
when in the linker of formula (II) or formula (III), n=1 or s=1; the platinum (II) biradical is attached to one molecule of linker of formula (II) or formula (III), thereby forming two COO—Pt bonds with the same linker molecule; and
when in the linker of formula (II) or formula (III), n=0 or s=0; the platinum (II) biradical is attached to two independent linker molecules of formula (II) or formula (III), thereby forming a COO—Pt bond with each of these two linker molecules; and
being at least 45% of the linkers L of formula (II) or formula (III) in the form of free carboxyl groups.

2. The conjugate according to claim 1, having a surface electrostatic absolute charge of at least 25 mV under physiological conditions.

3. The conjugate according to claim 2, wherein X represents —$(CH_2)_m$—and Y represents —$(CH_2)_r$—, wherein m represents a value from 2 to 10 with the condition that m+n represents a value from 2 to 10; and r represents a value from 2 to 10 with the condition that r+s represents a value from 2 to 10.

4. The conjugate according to claim 2, wherein NP is a gold nanoparticle.

5. The conjugate according to claim 2, wherein the nanoparticle is a nanosphere having a diameter from 4 to 20 nm.

6. The conjugate according to claim 2, which has colloidal stability in a physiological medium.

7. The conjugate according to claim 2, wherein in the linker of formula (II), n=0; and in the linker of formula (III), s=0.

8. The conjugate according to claim 3, wherein in the linker of formula (II), n=0 and m=10; and in the linker of formula (III), p=2, s=0 and r=4.

9. The conjugate according to claim 2, wherein A is a platinum (II) biradical of formula (IV).

10. A process for the preparation of a conjugate of formula (I) as defined in claim 1, comprising the following steps:
a) reacting a gold, silver or platinum nanoparticle NP with an excess of a compound selected from the group consisting of formula (IIa), formula (IIIa), a stereoisomer, and a salt of any of the formulas (IIa) and (IIIa), in an aqueous solution to give rise to an intermediate conjugate

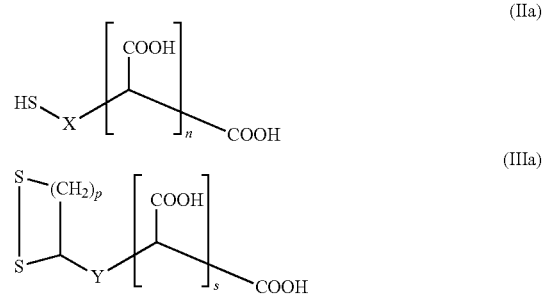

(IIa)

(IIIa)

wherein X, n, p, Y and s have the same meaning as in claim 1; and eliminating via dialysis the non-reactive molecules of the compound of formula (IIa) or formula (IIIa) of the colloidal solution after conjugation; and
b) reacting the intermediate conjugate obtained in step a) with an excess of a platinum (II) compound to give rise to a conjugate of formula (I) having colloidal stability, in an aqueous solution in the presence of a base, the platinum (II) compound being selected from the group consisting of formula (IVa), formula (Va), formula (VIa),

(IVa)

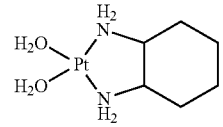

(Va)

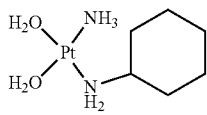

(VIa)

and a salt of any of the formulas (IVa), (Va) and (Via), including any of the stereoisomers thereof, followed by stopping the reaction to eliminate the excess of the platinum (II) compound when at least 45% of the linkers L of formula (II) or formula (III) in the resulting conjugate are in the form of free carboxyl groups.

11. A pharmaceutical composition comprising a conjugate of formula (I) as defined in claim 1 together with one or more pharmaceutically acceptable excipients.

12. The composition according to claim 11, which is administered by intravenous, subcutaneous or intramuscular injection.

13. A method for the treatment of cancer in a mammal, including a human, the method comprising administering to said mammal an effective amount of the conjugate of formula (I) as defined in claim 1, together with one or more pharmaceutically acceptable excipients.

14. The method of treatment according to claim 13, wherein the nanoparticle is a gold nanosphere having a diameter from 4 to 20 nm.

15. The method of treatment according to claim 13, wherein in the linker of formula (II) m=10, and in the linker of or formula (III) p=2 and r=4.

16. The method of treatment according to claim 13, wherein A is a platinum (II) biradical of formula (IV).

17. The conjugate according to claim 4, wherein the nanoparticle is a nanosphere having a diameter from 4 to 20 nm.

18. The conjugate according to claim 17, wherein A is a platinum (II) biradical of formula (IV).

* * * * *